(12) United States Patent
Pippin

(10) Patent No.: US 9,968,590 B2
(45) Date of Patent: May 15, 2018

(54) COMPOSITION AND METHOD FOR TREATMENT OF SYMPTOMS ASSOCIATED WITH VARIOUS SKIN CONDITIONS

(71) Applicant: THERACEUTIX, LLC, Exton, PA (US)

(72) Inventor: Douglas A. Pippin, Chester Springs, PA (US)

(73) Assignee: Theraceutix, LLC, Exton, PA (US)

(*) Notice: Subject to any disclaimer, the term of this patent is extended or adjusted under 35 U.S.C. 154(b) by 0 days. days.

(21) Appl. No.: 14/230,494

(22) Filed: Mar. 31, 2014

(65) Prior Publication Data

US 2014/0212362 A1    Jul. 31, 2014

Related U.S. Application Data

(63) Continuation of application No. PCT/US2012/057431, filed on Sep. 27, 2012.

(60) Provisional application No. 61/540,953, filed on Sep. 29, 2011.

(51) Int. Cl.
| | |
|---|---|
| *A61K 31/4164* | (2006.01) |
| *A61K 45/06* | (2006.01) |
| *C07D 233/64* | (2006.01) |
| *A61K 31/4172* | (2006.01) |

(52) U.S. Cl.
CPC ...... *A61K 31/4164* (2013.01); *A61K 31/4172* (2013.01); *A61K 45/06* (2013.01); *C07D 233/64* (2013.01)

(58) Field of Classification Search
None
See application file for complete search history.

(56) References Cited

U.S. PATENT DOCUMENTS

| | | | |
|---|---|---|---|
| 3,914,189 A | 10/1975 | Rudner et al. | |
| 4,447,431 A | 5/1984 | Sallmann | |
| 4,567,194 A | 1/1986 | Kroeplien et al. | |
| 6,416,788 B1 * | 7/2002 | Barr | A61K 8/02 424/489 |
| 7,598,280 B2 | 10/2009 | Augeri et al. | |
| 7,649,098 B2 | 1/2010 | Augeri et al. | |
| 7,812,174 B2 | 10/2010 | Wu et al. | |
| 7,825,142 B2 | 11/2010 | Augeri et al. | |
| 7,825,150 B2 | 11/2010 | Oravecz | |
| 2003/0207866 A1 | 11/2003 | Plucker et al. | |
| 2004/0110228 A1 | 6/2004 | McAlphine et al. | |
| 2007/0208063 A1 | 9/2007 | Augeri et al. | |
| 2008/0262241 A1 | 10/2008 | Wu et al. | |
| 2009/0030050 A1 | 1/2009 | Augeri et al. | |
| 2009/0068180 A1 | 3/2009 | Oravecz | |
| 2009/0312375 A1 | 12/2009 | Augeri et al. | |
| 2009/0318705 A1 | 12/2009 | Guohua et al. | |
| 2010/0076030 A1 | 3/2010 | Augeri et al. | |
| 2011/0071303 A1 | 3/2011 | Wu et al. | |
| 2011/0082178 A1 | 4/2011 | Augeri et al. | |
| 2011/0098482 A1 | 4/2011 | Wu | |

FOREIGN PATENT DOCUMENTS

| | | |
|---|---|---|
| RU | 2204392 C1 | 5/2003 |
| RU | 2247558 C1 | 3/2005 |
| SU | 1205764 A3 | 1/1986 |

OTHER PUBLICATIONS

International Preliminary Report on Patentability dated Apr. 1, 2014 in corresponding International Application No. PCT/US2012/057431.
Written Opinion and International Search Report for International Application No. PCT/US2012/057431 completed Nov. 26, 2012.
Thuvander et al., "Effects of Subchronic Exposure to Caramel Colour III on the Immune System in Mice", Fd Chem. Toxic, 1994, vol. 32, No. 1, pp. 7-13.
Houben et al., "Effects of the Colour Additive Caramel Colour III on the Immune System: A Study With Human Volunteers", Fd Chem. Toxic, 1992, vol. 30, No. 9, pp. 747-757.

* cited by examiner

*Primary Examiner* — Nicole P Babson
(74) *Attorney, Agent, or Firm* — RatnerPrestia

(57) ABSTRACT

Compositions containing imidazole-based compounds, and optionally, colloidal oatmeal, for the treatment, prevention, and management of symptoms, conditions, diseases, and disorders of the skin. Also, methods for the treatment, prevention, and management of symptoms, conditions, diseases, and disorders of the skin using compositions containing imidazole-based compounds, and optionally, colloidal oatmeal.

12 Claims, No Drawings

COMPOSITION AND METHOD FOR TREATMENT OF SYMPTOMS ASSOCIATED WITH VARIOUS SKIN CONDITIONS

CROSS-REFERENCE TO RELATED APPLICATIONS

This application is a continuation claiming benefit under 35 U.S.C. §§ 120 and 365(c) of PCT International Application No. PCT/US2012/057431, filed Sep. 27, 2012, and claiming benefit under 35 U.S.C. § 119(e) of U.S. Provisional Application No. 61/540,953, filed Sep. 29, 2011. The disclosures of PCT International Application No. PCT/US2012/057431 and U.S. Provisional Application No. 61/540,953 are incorporated herein by reference in their entirety.

FIELD OF THE INVENTION

This invention relates to compositions containing imidazole-based compounds, and optionally, colloidal oatmeal, and to methods of their use for the treatment, prevention, and management of symptoms, conditions, diseases, and disorders of the skin.

SUMMARY OF THE INVENTION

One aspect of the invention relates to a method of treating, managing, or preventing a dermatological or skin condition, which comprises topically administering to a subject in need thereof a therapeutically or prophylactically effective composition comprising an imidazole compound of the formula:

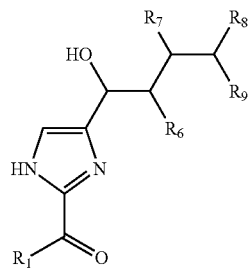

wherein:
$R_1$ is hydrogen, alkyl or aryl;
$R_6$ is $OR_{10}$ or $OC(O)R_{10}$;
$R_7$ is $OR_{11}$ or $OC(O)R_{11}$;
$R_8$ is $OR_{12}$ or $OC(O)R_{12}$; and
$R_9$ is hydrogen, $CH_2OR_{13}$ or $CH_2OC(O)R_{13}$; and each of $R_{10}$, $R_{11}$, $R_{12}$ and $R_{13}$ is independently hydrogen or lower alkyl,
and pharmaceutically, dermatologically, or cosmetically acceptable salts thereof.

Another aspect of the invention relates to a method of caring for skin, which comprises topically administering to the skin of a subject in need thereof a composition comprising the imidazole compound in an amount and for a time sufficient to effect a change in the skin.

Another aspect of the invention relates to a method of delivering or depositing a benefit agent onto skin, which comprises topically administering to the skin of a subject a composition comprising the imidazole compound contained in a dennatologically acceptable carrier.

Another aspect of the invention relates to a method of suppressing a dermatologic immune response in a patient in need thereof, comprising topically administering an effective composition comprising the imidazole compound contained in a dermatologically acceptable carrier.

Another aspect of the invention relates to a composition comprising an imidazole compound of the formula:

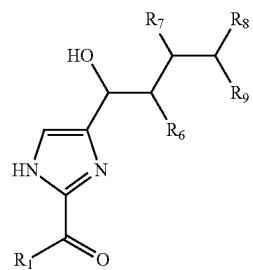

wherein:
$R_1$ is hydrogen, alkyl or aryl;
$R_6$ is $OR_{10}$ or $OC(O)R_{10}$;
$R_7$ is $OR_{11}$ or $OC(O)R_{11}$;
$R_8$ is $OR_{12}$ or $OC(O)R_{12}$; and
$R_9$ is hydrogen, $CH_2OR_{13}$ or $CH_2OC(O)R_{13}$; and each of $R_{10}$, $R_{11}$, $R_{12}$ and $R_{13}$ is independently hydrogen or lower alkyl,
and pharmaceutically, dermatologically, or cosmetically acceptable salts thereof.

Another aspect of the invention relates to compositions containing combinations of imidazole-based compounds and, optionally, colloidal oatmeal, and to methods of their use for the treatment, prevention, and management of inflammatory or immune-mediated symptoms, conditions, diseases, and disorders of the skin.

Another aspect of the invention relates to combinations of imidazole-based compounds and, optionally, colloidal oatmeal, and to methods of their use for the treatment, prevention, and management of various skin symptoms, conditions, diseases, and disorders.

Another aspect of the invention relates to combinations of imidazole-based compounds and colloidal oatmeal and to methods of their use for the treatment, prevention, and management of atopic dermatitis, seborrheic dermatitis, contact dermatitis, cutaneous sarcoidosis, drug induced photosensitivity, fixed drug eruptions, id reactions, bullous skin diseases, discoid lupus erythematosus, subacute cutaneous lupus, alopecia areata, sea bathers eruptions, psoriasis, dyshidrotic eczema, and pompholyx.

Another aspect of the invention relates to compositions and methods for treating inflammatory and/or immune-mediated dermatoses with imidazole-based compounds and combinations of imidazole-based compounds and colloidal oatmeal.

Another aspect of the invention relates to care, supplement, and pharmaceutical compositions containing imidazole-based compounds, colloidal oatmeal, and other ingredients used to treat disorders of the skin, as well as to compositions suitable for use in personal care applications, and in particular skin care compositions, which effectively deliver and/or deposit various benefit agents into and onto the skin.

Another aspect of the invention relates to compositions and methods for treating contact dermatitis.

These and further aspects of the claimed invention will now be explained in more detail.

DETAILED DESCRIPTION OF THE INVENTION

Definitions

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective" means sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective" can encompass a composition that improves overall prophylaxis or enhances the prophylactic efficacy of another prophylactic agent.

Unless otherwise indicated, a "therapeutically effective" means sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective" can encompass a composition that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted A, B, or C" has the same meaning as "optionally substituted A, optionally substituted B, or optionally substituted C."

It should be noted that a chemical moiety that forms part of a larger compound may be described herein using a name commonly accorded it when it exists as a single molecule or a name commonly accorded its radical.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences.

As used herein, the term "benefit agent" includes any active ingredient that is to be delivered into and/or onto the skin at a desired location, such as a cosmetic, care or pharmaceutical agent, and that is capable of providing a cosmetic, care, or therapeutic effect.

By "cosmetic agent," it is meant any ingredient that is appropriate for cosmetically treating, providing nutrients to, and/or conditioning the hair, nail, and/or skin via topical application.

By "pharmaceutical agent," it is mean any drug that is either hydrophobic or hydrophilic in nature and appropriate for topical use.

As used herein "medicament agents" include those agents capable of promoting recovery from injury and illness.

As used herein "pharmaceutically, dermatologically, or cosmetically acceptable" means that the ingredients which the term describes are suitable for use in contact with the skin without undue toxicity, incompatibility, instability, irritation, allergic response, and the like.

Other than where otherwise indicated, or where required to distinguish over the prior art, all numbers expressing quantities of ingredients herein are to be understood as modified in all instances by the term "about". As used herein, the words "may" and "may be" are to be interpreted in an open-ended, non-restrictive manner. At minimum, "may" and "may be" are to be interpreted as definitively including, but not limited to, the composition, structure, or act recited.

As used herein, and in particular as used herein to define the elements of the claims that follow, the articles "a" and "an" are synonymous and used interchangeably with "at least one" or "one or more," disclosing or encompassing both the singular and the plural, unless specifically defined herein otherwise. The conjunction "or" is used herein in both in the conjunctive and disjunctive sense, such that phrases or terms conjoined by "or" disclose or encompass each phrase or term alone as well as any combination so conjoined, unless specifically defined herein otherwise.

The description of a group or class of materials as suitable or preferred for a given purpose in connection with the invention implies that mixtures of any two or more of the members of the group or class are equally suitable or preferred. Description of constituents in chemical terms refers unless otherwise indicated, to the constituents at the time of addition to any combination specified in the description, and does not necessarily preclude chemical interactions among the constituents of a mixture once mixed. Steps in any method disclosed or claimed need not be performed in the order recited, except as otherwise specifically disclosed or claimed.

Changes in form and substitution of equivalents are contemplated as circumstances may suggest or render expedient. Although specific terms have been employed herein, such terms are intended in a descriptive sense and not for purposes of limitation.

Methods of Treatment

The general form of treatment for dermatoses according to the invention is chemical therapy by topical administration of the benefit agent or agents. Topical medications may be delivered to the affected site by means including but not limited to baths, soaps, shampoos, wet dressings or soaks, powders, pastes, tinctures, shake lotions, aerosols, foams, medicated tape, transdermal devices, creams, ointments, oils, and emulsions.

Generally, the composition is topically applied to the affected skin areas in a predetermined or as-needed regimen to bring about improvement, it generally being the case that gradual improvement is noted with each successive application. Insofar as has been determined based upon studies to date, no adverse side effects are encountered.

In treating atopic dermatitis, psoriasis, eczema, or any of the conditions or indications disclosed herein, an ointment or lotion according to aspects of the invention containing 0.01% to 10% by weight of the imidazole compound and, optionally, 0.01% to 25% of colloidal oatmeal is applied to the affected area of the skin. . The upper limit of the imidazole compound may preferably be 9%, 8%, 7%, 6%, 5%, 4%, 3%, 2.5%, 2%, or even 1.5% by weight of the ointment or lotion, and the lower limit of the imidazole compound may preferably be 0.01%, 0.05%, 0.1%, 0.2%, 0.3%, 0.4%, or even 0.5% by weight of the ointment or lotion. Preferably the ointment or lotion comprises 1.0% by weight of the imidazole compound. The upper limit of the colloidal oatmeal may preferably be 25%, 20%, 15%, 10%, 9%, 8%, 7%, 6%, 5%, 4%, 3%, 2.5%, 2%, or even 1.5% by weight of the ointment or lotion, and the lower limit of the colloidal oatmeal may preferably be 0.01%, 0.05%, 0.1%, 0.2%, 0.3%, 0.4%, or even 0.5% by weight of the ointment or lotion. Preferably the ointment or lotion comprises 1.0% by weight of the colloidal oatmeal. The patient may be treated, for example, daily for two to four weeks with a dosage amount of 5 mg to 10 mg of imidazole compound and 5 mg to 10 mg of colloidal oatmeal a day. The topically effective amounts of imidazole compound are typically 0.5% to 2% by weight and of the colloidal oatmeal 0.5% to 2% by weight in an ointment or lotion and are applied one to three times a day for a period of time, typically weeks, to effectively treat the dermatoses.

Under certain circumstances, it is desirable to administer the imidazole compound and colloidal oatmeal simultaneously with other dermatologically active agents. The precise amount of imidazole compound and colloidal oatmeal used alone or with other dermatologic agents varies depending, for example, on the condition for which the composition is administered. The amount, route of administration and dosing schedule will depend upon factors such as the specific indication to be treated, prevented, or managed, and the age, sex and condition of the patient. The roles played by such factors are well known in the art, and may be accommodated by routine experimentation. One skilled in the art can adjust the dosage forms to achieve the desired therapeutic levels.

Depending on the specific tissue to be treated, additional components may be used prior to, in conjunction with, or subsequent to treatment with active ingredients of the invention. For example, penetration enhancers may be used to assist in delivering active ingredients to the tissue.

Another embodiment of the present invention is directed to a method for depositing a benefit agent onto the skin to a desired location on a human or animal. While the frequency and amount of the benefit agent-containing composition to be applied will depend upon, for example, the type and amount of benefit agent available, the intended usage of the final composition, i.e. therapeutic versus maintenance regimen, and the sensitivity of the individual user to the composition, typically the benefit agent-containing composition of the present invention should be topically applied to affected body parts at regular intervals, and preferably twice daily, in the morning and evening. The composition may be applied more frequently during the initial stages of treatment, until the desired effect is achieved, then less frequently when maintenance is desired.

Conditions Treated

The methods according to the invention can be used to treat a variety of skin conditions, which result in inflammation or erythema. For example, inflammation or erythema can result from external causes such as sun or wind burn or irritating soaps or cleansers. It is also known that inflammation and erythema can be caused from inherent conditions such as rosacea, atopic dermatitis, or allergic skin reactions. The method according to the invention can be used to treat inflammation and/or erythema caused by both external and inherent conditions.

Another aspect of the invention relates to combinations of imidazole-based compounds and colloidal oatmeal and to methods of their use for the treatment, prevention, and management of atopic dermatitis, seborrheic dermatitis, contact dermatitis, cutaneous sarcoidosis, drug induced photosensitivity, fixed drug eruptions, id reactions, bullous skin diseases, discoid lupus erythematosus, subacute cutaneous lupus, alopecia areata, sea bathers eruptions, psoriasis, dyshidrotic eczema, and Pompholyx. This list of examples of dermatological conditions, for which the therapy as proposed in this application is useful, does not limit the present invention to these indications, since there may be other dermatological conditions not mentioned here where combinations of imidazole-based compounds and colloidal oatmeal may also be effective. Thus, further non-limiting examples of conditions to which the present invention may be applied include:

(a) dermatologic allergies, such as contact dermatitis, photoallergic dermatitis; industrial dermatoses caused by exposure to a variety of compounds used by industry that are contact irritants; atopic eczema (infantile and adult), dermatoses caused by drugs and nummular eczema;

(b) immune-mediated skin diseases, suchbullous pemphigoid, pemphigus vulgaris, necrotizing vasculitis, lupus erythematosus (discoid and systemic), dermatitis herpetiformis;

(B2) immune, non-immune, or autoimmune urticarias such as allergic urticaria, chronic idiopathic urticaria, solar urticaria, cholinergic urticaria, pressure urticaria, cold urticaria, dermatographia, and pruritic urticarial papules and plaques of pregnancy (PUPPP);

(B3) mastocytosis;

(c) pruritic dermatoses, such as winter, senile, and essential pruritus, pruritus ani, external otitis, and genital pruritus;

(d) vascular dermatoses, such as erythema multiforme, erythema nodosum, stasis dermatitis, purpuric dermatoses such as thrombocytopenic purpura and Henoch- Schonlein purpura, ecchymoses, stasis purpura, primary and secondary telangiectases;
(e) seborrheic dermatitis, acne, and rosacea;
(f) papulosquamous dermatoses: such as psoriasis, pityriasis rosea, lichen planus;
(g) bacterial dermatoses, such as pyoderma, impetigo, ecthyma, folliculitis, furuncles styes, carbuncles, sweat gland infections, erysipelas, erythrasma, infected ulcers, and infected eczematoid dermatitis;
(h) systemic bacterial infections with skin manifestations, such as scarlet fever, granuloma inguinale, chancroid, tuberculosis, leprosy, gonorrhea, rickettsial diseases, actinomycosis, syphilis;
(i) viral skin infection, such as those caused by herpes simplex virus, Kaposi's varicelliform eruption, zoster, chickenpox, smallpox, vaccinia, cowpox, warts, molluscum contagiosum, lymphogranuloma venereum, exanthematous diseases such as German measles, roseola and erythema infectiosum;
(j) mycolic skin infections, such as tinea (superficial fungal infections of the skin in various body sites), sporotrichosis, North American blastomycosis;
(k) granulomatous dermatoses, such as sarcoidosis, granuloma annulare, silica induced granulomas;
(l) parasitic skin infections, such as scabies, pediculosis;
(m) bullous dermatoses;
(n) exfoliative dermatitis, primary and secondary;
(o) pigmented dermatoses, such as chloasma (melasma) and vitiligo;
(p) collagen diseases, such as lupus erythematosus, scleroderma, dermatomyositis;
(q) dermatoses due to internal diseases, such as Kaposi's sarcoma, pyoderma gangrenosum associated with ulcerative colitis, ulcers due to diabetes, xanthomas;
(r) diseases of mucous membranes, such as aphthous ulcers;
(s) dermatoses due to physical agents, such as sunburns and radiation; and
(t) photosensitive dermatoses of the exogenous-type, such as drug-induced photodermatitis, contact dermatitis with photoallergic components, and of the endogenous-type, such as porphyrias, collagen vascular disorders such as lupus erythematosus, dermatomyositis, and polymorphous light eruptions.

Contact dermatitis is a steroid responsive condition and is caused by plant saps (poison ivy, etc) and chemicals. About 80% are irritant type while 20% are allergic. There are over 85,000 chemicals estimated to exist in the modern environment. Any might cause contact dermatitis. The most common allergic sensitizers are nickel sulfate, fragrances, thimerosal, quarternium-15, neomycin sulfate, formaldehyde, bacitracin, thiuram mix, balsam of Peru, cobalt chloride, p-phenylenediamine, and carba mix. Other steroid responsive dematoses might include seborrheic dermatitis, diaper rash, and bullous skin diseases such as bullous pemphigoid.

Further examples of diseases and disorders include ankylosing spondylitis, asthma (e.g., bronchial asthma), atopic dermatitis, Behcet's disease, graft-vs-host disease, Kawasaki syndrome, lupus erythematosus, multiple sclerosis, myasthenia gravis, pollinosis, psoriasis, psoriatic arthritis, rheumatoid arthritis, scleroderma, transplant rejection (e.g., of organ, cell or bone marrow), type 1 diabetes, and uveitis. Additional diseases and disorders include Addison's Disease, anti-phospholipid syndrome, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, pemphigoid, pemphigus vulgaris, pernicious anemia, polyarteritis nodosa, primary biliary cirrhosis, primary sclerosing cholangitis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, ulcerative colitis, and Wegener's granulomatosis.

Further indications addressed by the compositions and methods of the invention include, for example, immunosuppression (e.g., employing one or more agents such as cyclosporin A, OKT3, FK506, mycophenolate mofetil (MMF), azathioprine, corticosteroids (such as prednisone), antilymphocyte globulin, antithymocyte globulin, and the like), inflammatory disease therapy (e.g., employing disease-modifying agents (such as antimalarials, methotrexate, sulfasalazine, mesalamine, azathioprine, 6-mercaptopurine, metronidazole, injectable and oral gold, D-penicillamine, and the like), corticosteroids, non-steroidal antiinflammatory drugs (such as aspirin, sodium salicylate, magnesium salicylate, choline magnesium salicylate, salicylsalicylic acid, ibuprofen, naproxen, diclofenac, diflunisal, etodolac, fenoprofen calcium, fluriprofen, piroxicam, indomethacin, ketoprofen, ketorolac tromethamine, meclofenamate, meclofenamate sodium, mefenamic acid, nabumetone, oxaprozin, phenyl butyl nitrone (PBN), sulindac, tolmetin, and the like), and the like), anti-cancer therapy (e.g., employing one or more agents such as alkylating agents (such as mechlorethamine, chlorambuccil, ifosfamide, melphalan, busulfan, carmustine, lomustine, procarbazine, dacarbazine, cisplatin, carboplatin, and the like), antimetabolites (such as methotrexate, mercaptopurine, thioguanine fluorouracil, cytarabine, and the like), hormonal agents (such as testosterone propionate, fluoxymesterone, flutamide, diethylstilbestrol, ethinyl estradiol, tamoxifen, hydroxyprogesterone caproate, medroxyprogesterone, megestrol acetate, and the like), adrenocorticosteroids (such as prednisone), aromatase inhibitors (such as amino glutethimide), leuprolide, goserelin acetate, biological response modifiers (such as interferon-.alpha.2a, interferon-.alpha.2b, interleukin-2, and the like), peptide hormone inhibitors (such as octreotide acetate), natural products (such as vinblastine, vincristine, vinorelbine, paclitaxel, dactinomycin, daunorubicin, idarubicin, doxorubicin, etoposide, plicamycin, mitomycin, mitoxantrone, bleomycin, hydroxyurea, mitotane, fludarabine, cladribine, and the like), supportive agents (such as allopurinol, mesna, leucovorin, erythropoietin, filgrastim, sargramostim, and the like), and the like, anti-microbial therapy (e.g., employing one or more agents such as celftriaxone, TMP-SMZ, penicillin, aminoglycosides, vancomycin, gentamicin, rifampin, imipenem, clindamycin, metronidazole, tetracycline, erythromycin, sulfonamide, streptomycin, ampicillin, isoniazid, pyrazinamide, ethambutol, and the like), anti-fungal therapy (e.g., employing agents such as amphotericin B, griseofulvin, myastatin, flucytosine, natamycin, antifungal imidazoles (e.g., clotrimazole, miconazole, ketoconazole, fluconazole, itraconazole, and the like), and the like, anti-retroviral therapy (e.g., employing agents such as protease inhibitors (such as Invirase, Ritonavir, Crixivan, and the like), zidovudine, didanosine, zalcitabine, stavudine, viramune, and the like), and treatment of cellular proliferative diseases (e.g., oncolytic viral therapy employing naturally occurring and/or modified oncolytic viruses such as reovirus, adenovirus, seneca valley virus, vesicular stomatitis virus, poliovirus, vacina virus, herpes virus and the like), and treatment of opportunistic infections and malignancies (e.g., anti-AIDS treatment, employing agents such as pentamidine, trimethoprim/sulfamethoxazole, primaquine, atovaquone, clarithromycin, clofazimine, ethambutol, rifampin, amikacin, ciprofloxacin, pyrimethamine, amphotericin B, ganciclovir, foscarnet, fluconazole, ketoconazole, acyclovir, and the like).

Benefit Agents

A first element of the compositions and methods according to aspects of the invention is an imidazole compound of the formula:

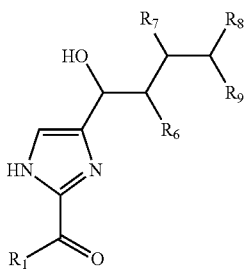

wherein:

$R_1$ is hydrogen, alkyl or aryl;
$R_6$ is $OR_{10}$ or $OC(O)R_{10}$;
$R_7$ is $OR_{11}$ or $OC(O)R_{11}$;
$R_8$ is $OR_{12}$ or $OC(O)R_{12}$; and
$R_9$ is hydrogen, $CH_2OR_{13}$ or $CH_2OC(O)R_{13}$; and each of $R_{10}$, $R_{11}$, $R_{12}$ and $R_{13}$ is independently hydrogen or lower alkyl.

The compounds of the preceding formula of the present invention may also be present in the form of pharmaceutically, dermatologically, or cosmetically acceptable salts thereof that can be made by conventional techniques.

Pharmaceutically, dermatologically, or cosmetically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide.

Pharmaceutically, dermatologically, or cosmetically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

In particular embodiments, the imidazole compound is 2-acetyl-4-tetrahydroxybutylimidazole (THI). THI is a component of caramel color III and has been identified as a sphingosine-1-phosphate lyase antagonist. Sphingosine-1-phosphate (S1P) is a bioactive molecule with effects on multiple organ systems. Sphingosine-1-phosphate lyase is a vitamin B6-dependent enzyme localized in the membrane of the endoplasmic reticulum. Van Veldhoven and Mannaerts, J. Biol. Chem. 266:12502-12507 (1991); Van Veldhoven and Mannaerts, Adv. Lipid. Res. 26:69 (1993). The polynucleotide and amino acid sequences of human SP1 lyase and its gene products are described in PCT Patent Application No. WO 99/16888.

THI inhibits S1P lyase activity when administered to mice. Schwab, S. et al., Science 309:1735-1739 (2005). Administration of the compound to rats and mice induces lymphopenia and causes the accumulation of mature T cells in the thymus. See, e.g., Schwab, supra; Pyne, S. G., ACGC Chem. Res. Comm. 11:108-112 (2000); Gugasyan, R., et al., Immunology 93(3):398-404 (1998); Halweg, K. M. and Büchi, G., J. Org. Chem. 50:1134-1136 (1985); U.S. Pat. No. 4,567,194 to Kroeplien and Rosdorfer. Still, there are no known reports of THI having an immunological effect in animals other than mice and rats. Although U.S. Pat. No. 4,567,194 alleges that THI and some related compounds may be useful as immunosuppressive medicinal agents, studies of the compound in humans have found no immunological effects. See Thuvander, A. and Oskarsson, A., Fd. Chem. Toxic. 32(1):7-13 (1994); Houben, G. F., et al., Fd. Chem. Toxic. 30(9):749-757 (1992).

Compounds of the invention may contain one or more stereocenters, and can exist as racemic mixtures of enantiomers or mixtures of diastereomers. This invention encompasses stereomerically pure forms of such compounds, as well as mixtures of those forms. Stereoisomers may be asymmetrically synthesized or resolved using standard techniques such as chiral columns or chiral resolving agents. See, e.g., Jacques, J., et al., Enantiomers, Racemates and Resolutions (Wiley Interscience, New York, 1981); Wilen, S. H., et al., Tetrahedron 33:2725 (1977); Eliel, E. L., Stereochemistry of Carbon Compounds (McGraw Hill, NY, 1962); and Wilen, S. H., Tables of Resolving Agents and Optical Resolutions, p. 268 (E. L. Eliel, Ed., Univ. of Notre Dame Press, Notre Dame, Ind., 1972). This invention further encompasses stereoisomeric mixtures of compounds disclosed herein. It also encompasses configurational isomers of compounds disclosed herein, either in admixture or in pure or substantially pure form.

Compounds of the invention can be prepared by methods known in the art (e.g., by varying and adding to the approaches described in Pyne, S. G., ACGC Chem. Res. Comm. 11:108-112 (2000); Halweg, K. M. and Büchi, G., J. Org. Chem. 50:1134-1136 (1985)). Compounds can also be made by the methods disclosed below and variants thereof, which will be apparent to those of ordinary skill in the art.

The compositions according to the invention preferably contain the imidazole-based compound in an amount of 0.001% to 10%, more preferably 0.5% to 2%, and most preferably about 1% by weight of the composition. The imidazole-based compound may also preferably be included in an amount of 0.01% to 10%, 0.1% to 10%, 0.1% to 9%, 0.1% to 8%, 0.1% to 7%, 0.1% to 6%, 0.1% to 5%, 0.2% to 5%, 0.3% to 5%, 0.4% to 5%, 0.5% to 5%, 0.5% to 4%, and 0.5% to 3% by weight of the composition.

A further element of preferred compositions and methods according to aspects of the invention is colloidal oatmeal. Oatmeal has been used as a soothing agent to relieve itch and irritation associated with various xerotic dermatoses. In 1945, a ready to use colloidal oatmeal, produced by finely grinding the oat and boiling it to extract the colloidal material, became available. Today, colloidal oatmeal is available in various dosage forms from powders for the bath to shampoos, shaving gels, and moisturizing creams. Currently, the use of colloidal oatmeal as a skin protectant is regulated by the U.S. Food and Drug Administration (FDA) according to the Over-The-Counter Final Monograph for Skin Protectant Drug Products issued in June 2003. Its preparation is also standardized by the United States Pharmacopeia.

The many clinical properties of colloidal oatmeal derive from its chemical polymorphism. The high concentration in starches and beta-glucan is responsible for the protective and water-holding functions of oat. The presence of different types of phenols confers antioxidant and anti-inflammatory activity. Some of the oat phenols are also strong ultraviolet absorbers. The cleansing activity of oat is mostly due to saponins. Its many functional properties make colloidal oatmeal a cleanser, moisturizer, buffer, as well as a soothing and protective anti-inflammatory agent. Colloidal oatmeal may act at the site of application to control the osmotic pressure of water with respect to the skin and permits adequate water to enter into the stratum corneum. Oatmeal may leave an occlusive film on the skin that serves to hold in moisture, which protects the skin against irritation and acts as an antipruritic.

Colloidal oatmeal includes the powder resulting from the grinding and further processing of whole oat grain meeting United States Standards for Number 1 or Number 2 oats. A suitable colloidal oatmeal has a particle size distribution as follows: not more than 3 percent of the total particles exceed 150 micrometers in size and not more than 20 percent of the total particles exceed 75 micrometers in size. Examples of suitable colloidal oatmeals include, but are not limited to, "Tech-O" colloidal oatmeals (e.g., Tech-O #11-065 colloidal oatmeal) available from the Beacon Corporation and colloidal oatmeals available from Quaker. A USP grade of colloidal oatmeal suitable for use in this invention may be obtained under the mark "Tech-O" from Beacon CMP Corporation, 611 Springfield Road, Kenilworth, N.J. 07033.

The compositions may further contain one or more benefit agents or pharmaceutically-acceptable salts thereof. The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed. In addition, the compounds, which are identified below as being suitable for use as benefit agents, may be used in an amount over and above the amount that they may be used for other purposes in the compositions of the invention.

Further benefit agents useful in the methods and compositions of the invention include antipruritics, emollients, antiseptics, antifungals, antiinflammatories, immunosuppressants, psoriasis agents, anti-cancer agents, antibiotics, antiparasitics, antioxidants, antibacterials, antimicrobials, antiretrovirals, moisturizers, sunscreens, NSAIDs, hormones, steroids, analgesics, antihistamines, and antipyretics. The following chemotherapeutic agents used to treat dermatoses are not comprehensive but rather consist of examples of commonly used groups of drugs. The antihistamines added to the topical compositions are typically from the structural classes of ethylenediamines, aminoalkylethers, and alkylamines. Among the ethylenediamine group are such antihistamines as antazoline phosphate, clemizole hydrochloride, chlorcyclizine hydrochloride, chlorothen, methapheniline hydrochloride, dorastine hydrochloride, methdilazine hydrochloride, promethazine hydrochloride, pyrathiazine hydrochloride, pyrilamine maleate, quinetolate, thenaldine, thenyldiamine hydrochloride, thonzylamine hydrochloride, tripelennamine, and zolamine hydrochloride. Among the aminoalkylether group are such antihistamines as chlorphenoxamine hydrochloride, carbinoxamine maleate, clemastine, diphenhydramine hydrochloride, diphenylpyraline hydrochloride, doxylamine succinate, and pyroxamine maleate. Among the alkamine group are such antihistamines as azatadine maleate, bromdiphenhydramine hydrochloride, cyproheptadine hydrochloride, dimethindene maleate, phenindamine tartrate, pheniramine maleate, brompheniramine maleate, dexbrompheniramine maleate, chlorpheniramine maleate, dex-chlorpheniramine maleate, closiramine, cycliramine maleate, mianserin hydrochloride, pyrrobutamine phosphate, terfenadine, and triprolidine hydrochloride. Besides the above, some compositions in structural groups, which groups are not primarily antihistamines such as phenothiazines, piperidines, and piperazines, have antihistaminic characteristics. These groups include promethazine, astemizole, fexofenadine, loratadine, desloratadine, terfenadine, cetirizine, and meclizin, which are antihistaminic.

Another active ingredient used in the formulations hereof is the employment of a topical anesthetic. While some of these topical anesthetic compounds are structurally related to the antihistamines in the preceding paragraph, the compounds take on a disinct role in preparations described. The first group are esters of benzoic acid and diethylaminoethyl alcohols, namely, benzocaine, chloroprocaine, procaine, and tetracaine. Other synthetic anesthetic compounds, which are not esters of benzoic acid and are pharmacologically grouped together, are bupivacaine, dibucaine, lidocaine, mepivacaine, and prilocaine. Besides these two groups, the compounds of etidocaine and pramoxine are also applicable. In one of the topical spray formulations described below the anesthetic, pramoxine hydrochloride, comprises up to 1.0 percent by weight thereof.

Corticosteroids are a group of agents used to treat inflammation of the skin having many different etiologies. Examples of indications in which systemically administered corticosteroids are employed as therapeutics include psoriasis, erythema nodosum leprosum, discold lupus erythematosus, urticaria, different types of pruritis, pemphigus and keloids. Antihistamines are a group of agents having an antipruritic effect. They include alkylamines, phenothiazines, ethylenediamine, ethanolamine, and piperazine. Retinoids are synthetic and natural forms of vitamin A, including isotretinoin and etretinate. Retinoids are used to treat acne vulgaris or rosacea and psoriasis. Antimicrobial compounds include antibiotic, antibacterial, antifungal, antiviral, and antiparasitic agents.

In addition to the imidazole-based compound and colloidal oatmeal, the benefit agents comprising topical preparations used according to the invention may also comprise:
(a) anti pruritic agents, which relieve itching, such as 0.25% menthol, 0.5% phenol, 2% camphor and 2-10% coal tar solutions;
(b) keratoplastic agents, which increase the thickness of the horny layer of the skin, such as 1-2% salicylic acid;
(c) emollients, which often soften surface layers of skin, such as petrolatum, nivea oil and mineral oil;
(d) antiseptics, which inhibit and/or destroy fungi and/or bacteria, such as 3% Vioform, 3-10% ammoniated mercury, antifungal agents such as Whitfields ointment, antibiotics such as 3% terramycin, 0.5% neomycin, 0.1% garamycin and 3% aureomycin;
(e) antieczematous agents, which remove oozing and vesicular excretions, such as Burows solution, soaks or packs, 2-5% coal tar solutions and 0.5-2% hydrocortisone;
(f) keratolytic agents, which remove or soften the horny layer of the skin, such as 4-10% salicylic acid, 2-4% resorcinol and 4-10% sulfur; and
(g) antiparasitics, which inhibit or destroy infestations by parasites, such as Kewell cream for scabies and pediculosis and Eurax lotion for scabies.

Further examples of suitable benefit agents include, but are not limited to: depigmentation agents; reflectants; film forming polymers; humectants; amino acids and their derivatives; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, antihistamines such as *Mandragora Vernalis, Tanacetum Parthenium* and the like; antiinfectives such as *Acacia Catechu, Aloe Barbadensis, Convallaria Majalis, Echinacea, Eucalyptus, Mentha Piperita, Rosa Canina, Sassafras Albidum*, and the like; inflammation inhibitors; anti-emetics; anticholinergics; vasoconstrictors; vasodilators; wound healing promoters; peptides, polypeptides and proteins; deodorants and anti-perspirants; medicament agents; skin emollients and skin moisturizers; skin firming agents, hair conditioners; hair softeners; hair moisturizers; vitamins; tanning agents; skin lightening agents; antifungals such as *Centaurea Cyanus, Kalmia Latifolia* and antifungals for foot preparations; depilating agents; shaving preparations; external analgesics; perfumes; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavenoids; sensates; anti-oxidants; skin conditioners; hair lighteners; chelating agents; cell turnover enhancers; coloring agents; pigments; sunscreens; anti-edema agents; collagen enhancers; and mixtures thereof.

Examples of suitable anti-edema agents nonexclusively include bisabolol natural, synthetic bisabolol, and mixtures thereof. Examples of suitable vasoconstrictors nonexclusively include horse chestnut extract, prickly ash, and mixtures thereof. Examples of suitable anti-inflammatory agents nonexclusively include benoxaprofen, centella asiatica, bisabolol, feverfew (whole), feverfew (parthenolide free), green tea extract, green tea concentrate, hydrogen peroxide, lycopene including "Lyc-o-Pen" available from LycoRed Natural Products Industries, Ltd., oat oil, chamomile, and mixtures thereof. Examples of collagen enhancers nonexclusively include vitamin A, vitamin C, and mixtures thereof. Examples of suitable skin firming agent nonexclusively include dimethylaminoethanol ("DMAE"). Examples of suitable antipruritics and skin protectants nonexclusively include betaglucan, feverfew, soy and derivatives thereof, bicarbonate of soda, colloidal oatmeal, surfactant based colloidal oatmeal cleanser, *Anagallis Arvensis, Oenothera Biennis, Verbena Officinalis*, and the like.

Examples of suitable reflectants nonexclusively include mica, alumina, calcium silicate, glycol dioleate, glycol distearate, silica, sodium magnesium fluorosilicate, and mixtures thereof. Suitable film forming polymers include those that, upon drying, produce a substantially continuous coating or film on the skin. Nonexclusive examples of suitable film forming polymers include acrylamidopropyl trimonium chloride/acrylamide copolymer; corn starch/acrylamide/sodium acrylate copolymer; polyquaternium-10; polyquaternium-47; polyvinylmethylether/maleic anhydride copolymer; styrene/acrylates copolymers; and mixtures thereof. Commercially available humectants which are capable of providing moisturization and conditioning properties to the composition are suitable for use in the present invention. Examples of suitable humectants nonexclusively include: water soluble liquid polyols selected from the group comprising glycerine, propylene glycol, hexylene glycol, butylene glycol, pentylene glycol, dipropylene glycol, and mixtures thereof; polyalkylene glycols; polyethylene glycol ether of methyl glucose; urea; fructose; glucose; honey; lactic acid; maltose; sodium glucuronate; and mixtures thereof.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, capryloyl collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; amino acids such as aspartic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof.

Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; milk protein; protease; serum protein; silk; sweet almond protein; wheat germ protein; wheat protein; alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A,C,D, E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth-10, methyl gluceth-20 chitosan, and mixtures thereof.

Examples of sunscreen agents nonexclusively include benzophenones, bornelone, butyl paba, cinnamidopropyl trimethyl ammonium chloride, disodium distyrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, Padimate O, red petrolatum, and mixtures thereof. Further examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3,3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof.

Examples of suitable anti-aging agents include, but are not limited to inorganic sunscreens such as titanium dioxide and zinc oxide; organic sunscreens such as octyl-methoxy cinnamates and derivatives thereof; retinoids; vitamins such as vitamin E, vitamin A, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, beta-phenylpyruvic acid; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof. Examples of suitable inflammation inhibitors nonexclusively includes hydrocortisone, *Fragaria Vesca, Matricaria Chamomilla*, and *Salvia Officinalis*. Other well-known antipruritic agents include phenol, camphor, menthol, hydro-cortisone, hydrocortisone acetate, camphorated metacresol, phenolated sodium, and mixtures thereof.

Other preferred benefit agents nonexclusively include DMAE, soy and derivatives thereof, colloidal oatmeal, sulfonated shale oil, olive leaf, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylmonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

One preferred type of benefit agent includes those therapeutic components that are effective in the treatment of seborrheic dermatitis and psoriasis as well as the symptoms associated therewith. Examples of such suitable benefits agents nonexclusively include zinc pyrithione, anthralin, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazole nitrate and any possible stereo isomers and derivatives thereof; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

Further examples of benefit agents are emollients, skin conditioning agents, humectants, preservatives, antioxidants, perfumes, chelating agents, or mixtures thereof. Emollients in the composition of the invention function have ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 acetyl ether, steareth-10, oleth-8, PPG-4 lauryl ether, vitamin E acetate, PEG-7 glyceryl cocoate, lanolin, cetyl alcohol, (e.g., Cetyl Alcohol NF available from Lotioncrafter LLC) octyl hydroxystearate, dimethicone (e.g., Xiameter® PMX-200 Silicone Fluid 100CS available from Dow Corning), and combinations thereof.

Examples of skin conditioning agents include, but are not limited to, olive leaf, sulfonated shale oil, elubiol, 6-(1-piperidinyl)-2,4-pyrimidinediamine-3-oxide, finasteride, ketoconazole, zinc pyrithione, coal tar, benzoyl peroxide, selenium sulfide, hydrocortisone, pramoxine hydrochloride, tricetylammonium chloride, polyquaternium 10, panthenol, panthenol triacetate, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, erthromycin, tretinoin, and mixtures thereof.

Polyhydric alcohols can be utilized as humectants in the compositions of the invention. The humectants aid in increasing the effectiveness of the emollient, reduce scaling, stimulate removal of built-up scale and improve skin feel. Suitable polyhydric alcohols include, but are not limited to, glycerol (also known as glycerin), polyalkylene glycols, alkylene polyols and their derivatives, including butylene glycol, propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof.

Examples of suitable preservatives for use in the compositions of the invention include the $C_1$-$C_4$ alkyl parabens and phenoxyethanol (e.g., Microcare® PE available from Thor Personal Care). Suitable antioxidants include butylated hydroxy toluene (BHT), ascorbyl palmitate, butylated hydroanisole (BHA), phenyl-[alpha]-naphthylamine, hydroquinone, propyl gallate, nordihydroquiaretic acid, vitamin E or derivatives of vitamin E, vitamin C and derivatives thereof, calcium pantothenic, green tea extracts and mixed polyphenols, and mixtures thereof. Any fragrance may be added to the compositions of the invention for aesthetic purposes. Suitable fragrances include, but are not limited to, eucalyptus oil, camphor synthetic, peppermint oil, clove oil, lavender, chamomile and the like.

In certain aspects of this invention, the compositions may include a chelating agent. Chelating agents which are useful in the compositions of present invention include ethylenediamine tetra acetic acid (EDTA) and derivatives and salts thereof, dihydroxyethyl glycine, tartaric acid, and mixtures thereof.

It is also envisioned that the composition of this invention could be combined with other agents topical anesthetics, for example, such as benzocaine or other caine type molecules, or even mild steroids such as hydrocortisone for enhanced anti-inflammatory activity.

Further benefit agents useful in the compositions and methods of the present invention include, but are not limited to:

antihistamine/antipruritic drugs, such as ethanolamines (e.g., diphenhydramine, diphenhydramine hydrochloride, clemastine, clemastine fumarate, and the like), ethylenediamines (e.g., brompheniramine, brompheniramine maleate, chlorpheniramine, chlorpheniramine maleate, dexchlorpheniramine maleate, triprolidine, triprolidine hydrochloride, and the like), phenothiazines (e.g., promethazine), piperidines (e.g., hydroxzine, hydroxyzine hydrochloride, terfenadine, astemizole, azatadine, azatadine maleate, and the like), cyproheptadine, cyproheptadine hydrochloride, loratidine, carbinoxamine maleate, diphenylpyraline hydrochloride, phenindamine tartrate, tripelennamine hydrochloride, methdilazine hydrochloride, trimprazine tartrate, and the like;

immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., CHI-621 and dacliximab), buspirone, castanospermine, CD-59 (complement factor inhibitor), 5-lipoxygenase inhibitor (e.g., CMI-392), phosphatidic acid synthesis antagonists, ebselen, edelfosine, enlimomab, galaptin, platelet activating factor antagonists, selectin antagonists (e.g., ICAM-4), interleukin-10 agonist, macrocylic lactone, methoxatone, mizoribine, OX-19, peptigen agents, PG-27, protein kinase C inhibitors, phosphodiesterase IV inhibitor, single chain antigen binding proteins, complement factor inhibitor, sialophorin, sirolimus, spirocyclic lactams, 5-hydroxytryptamine antagonist, anti-TCR monoclonal antibodies, CD5 gelonin and TOK-8801, and the like;

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antifungal agents (e.g., griseofulvin, keloconazole, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

antioxidants (e.g., N-acetylcsysteine, Vitamin A, Vitamin C, Vitamin E, .beta.-carotene, EUK-8, flavonoids, glutathione, .alpha.lipoic acid, melatonin, retinols, and the like);

anti-infectives (e.g., miconazole, vidarabine, inosine, pranobex, vidarabine, inosine prabonex, cefpimizole sodium), fradiomycin, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

psoriasis agents, such as 5-LO inhibitors (e.g., Wy-50295, Wy-49232, Lonapalene, RS-43179, MK-886, L-663536, ETH-615, DUP-654, Zileuton, epocarbazolin-A, and A-64077), 5-LO/CO inhibitors (e.g., BF-397, Tenidap, CP-309, and CP-66248), angiogenesis inhibitors (e.g., platelet factor 4), anticancer antibiotic (e.g., AGM-1470, and TNP-470), anti-inflammatory cytochrome P450 oxidoreductase inhibitors (e.g., DuP-630, and DuP-983), antiproliferative compounds (e.g., Zyn-Linker), arachidonic acid analogues (e.g., CD581, and CD554), arachidonic acid antagonists (e.g., Lonapalene, RS-43179, triamcinolone acetonide with penetration enhancer Azone, betamethasone dipropionate steroid wipe, G-202, Halobetasol propionate, ultravate, Halometasone, C-48401-Ba, and Sicorten), beta-glucan receptor antagonists, betamethasone steroid wipes, calcium metabolic moderators (e.g., Tacalcitol, Bonealfa, TV-02 ointment, Ro-23-6474, KH-1060, Calcipotriol, BMS-181161, BMY-30434, Dovonex, and Divonex), CD4 binding inhibitors (e.g., PIC 060), cell adhesion compounds (e.g., CY-726, VCAM-1, ELAM-1, and ICAM), cell adhesion inhibitors (e.g., selectin inhibitor, GM-1930), cellular aging inhibitors (e.g., Factor X), corticosteroids (e.g., Halobetasol propionate, ultravate, Halometasone, C-48401-Ba, and Sicorten), cyclosporin analogues (e.g., IMM-125), dihydrofolate reductase inhibitors (e.g., G-301, dichlorobenzoprim, methotrexate, and methotrexate in microsponge delivery system), E-selectin inhibitors (e.g., ISIS 4730), endogenous active form of vitamin D3 (e.g., Calcitriol, and Du-026325), fibroblast growth factor antagonists (e.g., Saporin mitotoxin, and Steno-Stat), fumagillin analogues (e.g., AGM-1470, and TNP-470), G-proteins and signal transduction compounds (e.g., CPC-A), gel formulations for acne (e.g., nicotinamide, N-547, and Papulex), growth hormone antagonists (e.g., Octreotide, Sandostatin, Lanreotide, angiopeptin, BIM-23014, and Somatuline), humanized antibodies (e.g., anti-CD4 antibody), hydroorotate dehydrogenase inhibitors (e.g., Brequinar sodium, bipenquinate, and DuP-785), ICAM-1 inhibitors (e.g., ISIS 939), IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, and FK-506), IL-2 receptor-targeted fusion toxins (DAB389IL-2), IL-8 receptors, immunostimulants (e.g., Thymopentin, and Timunox), immunosuppressants (e.g., XomaZyme-CD5 Plus, cyclosporine, Sandimmune, SR-31747, anti-CD 11, 18 MAb, Tacrolimus, Prograf, FK-506, and FK-507), immunosuppressive agents targeting FK506 (e.g., immunophilins, VX-10367, and VX-10428), immunotoxins MAb directed against CD antigen (e.g., XomaZyme-CD5 Plus), leukotriene antagonists (e.g., Sch-40120, Wy-50295, and Wy49232), leukotriene B4 antagonists (e.g., SC-41930, SC-50605, SC-48928, ONO-4057, LB-457, LY-255283, LY-177455, LY-223982, LY-223980, and LY-255253), leukotriene synthesis inhibitors (MK-886, and L-663536), lipase clearing factor inhibitors (e.g., 1-docosanol, and lidakol), lipid encapsulated reducing agent (e.g., Dithranol), liposomal gel (e.g., Dithranol), LO inhibitors (e.g., CD581, CD554, Masoprocol, and Actinex), lithium succinate ointments (e.g., lithium salts, and Efalith), LO/CO inhibitors (e.g., P-8892, P-8977, CHX-108, and FPL-62064), membrane integrity agonists (e.g., lithium salts, and Efalith), microtubule inhibitors (e.g., Posophyliotoxin-containing compound, and Psorex), octapeptide somatostatin analogues (e.g., Lanreotide, angiopeptin, BIM-23014, and Somatuline), oligonucleotides (e.g., ISIS 4730, ISIS 3801, ISIS 1939, and IL-1 inhibitors), peptide agonists (e.g., octapeptide, and peptide T), PKC inhibitors, phospholipase A2 compounds, pospholipase D compounds, photodynamic anticancer agents (e.g., 5-aminolevulinic acid, and 5-ALA), photodynamic therapies (e.g., benzoporphyrin derivative, synthetic chlorins, synthetic porphyrins, and EF-9), photosensitizer (e.g., Porfirmer sodium), PKC inhibitors (e.g., Safingol, and Kynac), platelet activating factor antagonists (e.g., TCV-309), platelet aggregation inhibitors (e.g., CPC-A), prodrug NSAIDs (e.g., G-201), prostaglandin agonist (e.g., eicosapentaenoic acid +gamma-linolenic acid combination, and Efamol Marine), protein inhibitors (e.g., SPC-103600, and SPC-101210), protein kinase C (PKC) inhibitors (e.g., Ro-31-7549, Ro-31-8161, and Ro-31-8220), protein synthesis antagonists (e.g., Calcitriol, Du-026325, LG-1069, LG-1064, AGN-190168, Namirotene, and CBS-211A), purine nucleoside phosphorylase inhibitors (e.g., BCX-34), radical formation agonists (e.g., benzoporphyrin derivative), recombinant antileukoproteinases (e.g., ALP-242), retinoids (e.g., BMY-30123, LG-1069, and LG-1064), retinoid derivatives (e.g., AGN-190168), rapamycin binding proteins (FKBP) (e.g., immunophilins, VX-10367, and VX-10428), second generation monoaromatic retinoids (e.g., Acitretin, and Neotigason), soluble IL-1, IL-4 and IL-7 receptors, somatostatin and somatostatin analogues (e.g., Octreotide, and Sandostatin), steroids, (e.g., AGN-191743), streptomyces anulatus isolates (e.g., epocarbazolin-A), superoxide dismutase (e.g., EC-SOD-B), thymidylate synthase inhibitors (e.g., AG-85, MPI-5002, 5-FU in biodegradable gel-like matrix, 5-FU and epinephrine in biodegradable gel-like matrix, and AccuSite), topical formulations (e.g., P-0751, and P-0802), transglutaminase inhibitors, tyrphostin EGF receptor kinase blockers (e.g., AG-18, and AG-555), VCAM-1 inhibitors (e.g., ISIS 3801), vitamin D analogues (e.g., Ro-23-6474, KH-1060, Calcipotriol, BMS-181161, BMY-30434, Dovonex, and Divonex), vitamin D3 analogues (e.g., Tacalcitol, 20 Bonealfa, TV-02 ointment), and vitamin D3 derivatives (e.g., 1,2-diOH-vitamin D3), and the like; and agents useful for the treatment of carcinomas (e.g., adriamycin, taxol, interleukin-1, interleukin-2 (especially useful for treatment of renal carcinoma), and the like, as well as leuprolide acetate, LHRH analogs (such as nafarelin acetate), and the like, which are especially useful for the treatment of prostatic carcinoma).

The amount of benefit agent to be included may vary depending upon, for example, the ability of the benefit agent to penetrate through the skin, the specific benefit agent chosen, the particular benefit desired, the sensitivity of the user to the benefit agent, the health condition, age, and skin condition of the user, and the like. In sum, the benefit agent is used in a "safe and effective amount," which is an amount that is high enough to deliver a desired skin benefit or to modify a certain condition to be treated, but is low enough to avoid serious side effects, at a reasonable risk to benefit ratio within the scope of sound medical judgment.

Formulations

The compositions of the present invention can be prepared and administered in a wide variety of topical forms. For topical formulations of the present invention, dermatologically acceptable carriers can be either solid or liquid. The compositions of this invention is preferably in the form of topical products that can be applied externally to the skin and can be prepared in accordance with conventional techniques known to those of ordinary skill in the art. The carrier may take a variety of physical forms such as, for example, creams, dressings, gels, lotions, ointments or liquids. One could also utilize this in a convenient spray applicator.

Typical carriers include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids.

The compositions according to the invention preferably contain an effective stabilizing amount of an emulsifier. Any emulsifier that is compatible with the components of the composition can be employed. Suitable emulsifiers include stearic acid, acetyl alcohol, stearyl alcohol, steareth 2, steareth 20, Acrylates/C10-30 alkyl Acrylate Crosspolymer Particularly preferred is PEMULEN TR-1 (CTFA Designation: Acrylates/10-30 Alkyl Acrylate Crosspolymer).

The composition of the invention may be in the form of an oil-in-water emulsion, a water-in-oil emulsion, or a dispersion. Liquid form preparations such as lotions or creams include solutions, suspensions, and emulsions, for example, water or DMSO/propylene glycol solutions. Liquid suspensions suitable for topical use can be made by dispersing the finely divided active component in an appropriate liquid with viscous material, such as natural or synthetic gums, resins, methycellulose, sodium carboxymethylcellulose, and other well-known suspending agents.

Also included are solid form preparations which are intended to be converted, shortly before use, to liquid form preparations for topical administration. Such liquid forms include solutions, suspensions, and emulsions. These preparations may contain, addition to the active component, colorants, flavors, fragrances, stabilizers, buffers, artificial and natural sweeteners, dispersants, thickeners, solubilizing agents, and the like.

To prepare dermally applicable formulations it is possible to use the previously mentioned substances and spreadable or liquid hydrocarbons such as Vaseline or paraffin or gels of alkanes and polyethylene, fats and oils of plant or animal origin, which may in part also be hydrated, or synthetic fats such as glycerides of fatty acids $C_8$-$C_{18}$, as well as beeswax, cetyl palmitate (e.g., Cutina® CP available from Cognis/BASF), wool wax, wool wax alcohols, fatty alcohols such as cetyl alcohol, stearyl alcohol, polyethylene glycols of molecular weight 200 to 20,000; liquid waxes such as isopropyl myristate, isopropyl stearate, ethyloleate; emulsifiers such as sodium, potassium, ammonium salts of stearic acid or palmitic acid as well as triethalolamine stearate, alkali salts of oleic acid, castor oil acid, salts of sulfurated fatty alcohols such as sodium lauryl sulphate, sodium cetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, partial fatty acid esters of polyoxyethylene sorbitan, sorbitol ethers of polyoxyethylene, fatty acid esters of polyoxyethylene, fatty alcohol ethers of polyoxyethylene, fatty acid esters of saccharose, fatty acid esters of polyglycerol, lecithin.

Examples of suitable esters nonexclusively include a branched $C_5$ to $C_{22}$ alkyl alcohol ester of an aromatic acid, a straight-chained or branched $C_5$ to $C_{22}$ alkyl acid esters of optionally ethyoxylated/propoxylated polyols having from about 3 carbon atoms to about 7 carbon atoms, a branched $C_5$ to $C_{22}$ alkyl alcohol esters of branched polyacids, a branched or straight-chained $C_5$ to $C_{22}$ alkyl acid esters of branched and/or unsaturated $C_5$ to $C_{22}$ alkyl alcohols, a branched or unsaturated $C_5$ to $C_{22}$ alkyl alcohol esters of an aromatic acid selected from the group consisting of adipic acid, succinic acid, maleic acid, sebacic acid, and mixtures thereof, polyether interrupted fatty acid esters, benzoic acid ester of heterogeneous alcohols having from about 8 carbon atoms to about 22 carbon atoms and mixtures thereof with straight-chained or branched $C_5$ to $C_{22}$ alkyl acid esters of optionally ethyoxylated/propoxylated polyols, benzoic acid esters of heterogeneous alcohols, and mixtures thereof. Further suitable esters are disclosed in U.S. Pat. No. 6,762,158, the entire disclosure of which is incorporated herein by reference.

Antioxidants that may for example be used are sodium metabisulphite, ascorbic acid, gallic acid, gallic acid alkyl ester, butylhydroxyanisol, nordihydroguaiacic acid, tocopherols as well as tocopherols .+-.synergitic substances that bind heavy metals through complex formation, for example lecithin, ascorbic acid, phosphoric acid). Conserving agents that may for example be considered are sorbic acid, p-hydroxybenzoic acid esters (for example lower alkyl esters), benzoic acid, sodium benzoate, trichloroisobutyl alcohol, phenol, cresol, benzethonium chloride and formalin derivatives.

Topical dosage forms include, but are not limited to, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). See also Cosmetic Model Formulae—A Compilation of Model Formulae for the Manufacture of Cosmetic Preparations (Henkel KGaA; 1988), the entirety of which is incorporated herein by reference. Transdermal dosage forms include "reservoir type" or "matrix type" patches, which can be applied to the skin and worn for a specific period of time to permit the penetration of a desired amount of active ingredients. Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

The pH of the inventive compositions may also be adjusted to improve delivery of one or more active ingredients. In another preferred embodiment, the compositions used in the methods of present invention contain a pH-buffering agent. Preferably, the amount of buffering agent should be that which would result in compositions having a pH ranging from about 4.5 to about 8.5, more preferably from about 5.5 to about 8.5, most preferably from about 6.5 to about 8.0. The buffering agent can be any of the known buffering agents commonly found in topical compositions provided that they are physically and chemically stable with the other ingredients of the composition. Suitable buffering agents include organic acids such as, but not intended to be restricted to, citric acid, malic acid, and glycolic acid.

Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

The topical compositions of the present invention may contain a water dispersible component, which is preferably a water soluble solvent. As used herein, the term "water dispersible component" shall mean a material that produces a uniform, clear or hazy, mixture when combined with at least a weight equivalent of water. Examples of suitable water dispersible components nonexclusively include polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-l-butanol, dimethyl isosorbide, and mixtures thereof. Most preferred water dispersible components include hexylene glycol, dimethyl isosorbide, polyethylene glycol-6 caprylic/capric glyceride, and mixtures thereof.

A further optional component of the compositions of the present invention is a volatile or nonvolatile liquid silicone. Examples of suitable silicones nonexclusively include the polydimethyl siloxanes and derivatives thereof such as hexamethylsiloxane, dimethicone, dimethiconol, and cyclomethicone, with cyclomethicone being preferred. Examples of suitable cyclomethicones nonexclusively include cyclotetradimethyl siloxane; cyclopentadimethyl siloxane, cyclohexadimethyl siloxane, cycloheptadimethyl siloxane, and mixtures thereof.

Further optional components of the compositions of the present invention are polymeric emulsifiers and/or thickeners. Examples of suitable polymeric emulsifiers nonexclusively include polyethylene glycol-30 dipolyhydroxystearate, dimethicone copolyol, substituted acrylates, and mixtures thereof. Examples of suitable hydrophilic thickeners nonexclusively include carbomers (e.g., Carbopol® Ultrez polymers available from Lubrizol Corp.; also various carbomer prodcts available from B. F. Goodrich), acrylate copolymers, hydroxyethylcellulose modified with cetyl ether groups, polyvinylmethyl ether/maleic anhydride (PVM/MA) decadiene crosspolymer, and copolymers and mixtures thereof. Examples of suitable acrylate copolymers nonexclusively include acrylate copolymers available from Rohm & Haas, acrylates/aminoacrylates copolymer, acrylates/steareth-20 itaconate copolymer, acrylates/ceteth-20 itaconate copolymer, acrylates/steareth-20 methacrylate copolymer, and copolymers and mixtures thereof.

The compositions of the present invention may also optionally contain a stability enhancer for the purpose of enhancing the stability of the benefit agent and/or the aesthetics of the composition. Generally, the stability enhancer may be selected from a nonionic emulsifier, an essentially non-foaming surfactant, or mixtures thereof. Examples of suitable nonionic emulsifiers include iso-ceteth-20, oleth-2, mixture of PEG-40 hydrogenated castor oil and trideceth-9, Poloxamer 184, laureth-4, sorbitan trioleate, polyoxyethylene-(2) oleyl ether, sorbitan stearate, cetearyl glucoside, glyceryl oleate, trideceth-9, polyethylene glycol-40 hydrogenated castor oil, and mixtures thereof.

Examples of suitable essentially non-foaming surfactants include non-foaming nonionic surfactants such as sucrose esters, e.g., sucrose cocoate, sucrose stearate and mixtures thereof. By "essentially non-foaming," it is meant that the surfactant, when used with the composition of the present invention, has a column height of less than about 20 mm as determined by the Ross-Miles Foam Generation Test. See 18 (I.) Oil & Soap 99-102 (1941)("Ross-Miles Test"), which is incorporated by reference herein. The composition may either be rinseable with water or may be wiped-off. Preferably, the essentially non-foaming surfactants are used in embodiments wherein the composition is rinseable with water.

The composition may also optionally contain a foaming surfactant. The foaming surfactant may be non-ionic, cationic, amphoteric, or anionic. By "foaming," it is meant that the surfactant, when used with the composition of the present invention, has a column height of foam greater than about 20 mm as determined by the Ross-Miles Test.

Preservatives for the formulations herein are benzoic acid and derivatives thereof, namely, butylparaben, ethylparaben, methylparaben, propylparaben, sodium benzoate, and mixtures thereof. Typical use of benzoic-acid-derived preservative is a mixture of methylparaben comprising up to 0.3 percent by weight of the treating composition and propylparaben comprising up to 0.1 percent by weight of the treating composition. Other useful preservatives include alcohol, benzalkonium chloride, benzethonium chloride, benzyl alcohol, bronopol, cetrimide, chlorhexidine, chlorobutanol, chlorocresol, cresol, glycerin, imidurea, phenol, phenoxyethanol, phenylethyl alcohol, phenylmercuric acetate, phenylmercuric borate, phenylmercuric nitrate, potassium sorbate, propylene glycol, sodium propionate, sorbic acid and thimerosal.

Among the inactive ingredients are surfactants and emulsifying agents. These ingredients take on importance as the use thereof improves absorption, coverage, appearance, and feel of the product. Some suitable emulsifying agents are acacia, anionic emulsifying wax, carbomer, carboxymethyl cellulose, cetostearyl alcohol, cetyl alcohol, cholesterol, diethanolamine, glyceryl monostearate, hydrous lanolin, hydroxyethyl cellulose, hydroxypropyl cellulose, hydroxypropyl methylcellulose, lanolin, lanolin alcohols, lecithin, methylcellulose, mineral oil and lanolin alcohols, monobasic sodium phosphate, monoethanolamine, nonionic emulsifying wax, oleic acid, poloxamer, polyoxyethylene alkyl ethers, polyoxyethylene castor oil derivatives, polyoxyethylene sorbitan fatty acid esters, polyoxyethylene stearates, propylene glycol alginate, sodium lauryl sulfate, sorbitan esters, stearic acid, triethanolamine, and xanthan gum. Frequently mixtures of complimentary surfactants are used in a given formulation.

Suitable anionic surfactants are lauryl sulfates, including sodium lauryl sulfate, triethanolamine lauryl sulfate, and ammonium lauryl sulfate; laureth sulfates,including sodium laureth sulfate, triethanolamine laureth sulfate, and ammonium laureth sulfate; sarcosines, including lauryl sarcosine, and sodium lauryl sarcosinate; sulfosuccinates, including disodium oleamine sulfosuccinate, and sodium dioctyl sulfosuccinate; and docusate sodium. The cationic surfactants are benzalkonium chloride, benzethonium chloride, and cetrimide. The nonionic surfactants are glyceryl monooleate, polyvinyl alcohol, sorbitan esters, povidone, crospovidone, polyoxyethylene fatty alcohols, polyoxyethylene sorbitol esters, and alkanolamides. Additionally, amphoteric detergents such as betaines, sultaines, and imidazolinium derivatives are used, and particularly ingredients such as cocamidopropyl betaine and sodium lauraminopropionate.

In ointment and cream preparations, emollients form a vehicle to carry the active ingredients to the site of the immune response and the associated dermatitis. The emollient group from which these carriers are selected include allantoin, cetostearyl alcohol, cetyl esters wax, cocoa butter, cholesterol, dimethicone, glycerin, glyceryl monostearate, isopropyl myristate, isopropyl palmitate, kaolin, lecithin, light mineral oil, mineral oil, mineral oil and lanolin alcohols, petrolatum, and petrolatum and lanolin alcohols.

The carrier can be any suitable aqueous dispersion material, cream, lotion, or ointment, which may include, for example hydrocolloids, plasdone, methyl cellulose, hydroxypropyl cellulose, lanolin, mineral oil, petroleum jelly, polyalkylene glycols such as polyethylene glycols, or mixtures thereof. The formulations may contain surfactants, antioxidants, and stabilizers such as benzoic acid, sorbic acid, parabens, butylated hydroxyanisole (BHA), butylated hydroxytoluene (BHT), vitamin E, sarcosonates, and the like.

The benefit agents can also be combined with astringents such as witch hazel, aluminum acetate, aluminum sulfate, zinc oxide, zinc acetate, sodium bicarbonate, and calamine. One of the functions of the formulations when applied to contact dermatitis is to remove the irritant material from the skin. This requires astringent activity, and the addition of aluminum acetate, zinc oxide, zinc acetate, sodium bicarbonate, calamine, witch hazel, zinc carbonate, and aluminum hydroxide may be employed to enhance this physical property.

A preferred carrier material includes water, glycerin, cetyl palmitate, mineral oil, caprylic/capric triglyceride, octyldodecanol, cetyl alcohol, glyceryl stearate, colloidal oat flour, dimethicone, PEG-40 stearate, carbomer, sodium hydroxide, phenoxy ethanol, caramel III coloring, DMDM hydantoin, and iodopropynyl butylcarbamate.

Glycerin, also called glycerol, acts as a humectant, skin protectant, and solvent present in all natural lipids (fats), whether animal or vegetable. Whether natural or synthetic, glycerin is a humectant and extremely hygroscopic, meaning it readily absorbs water from other sources, attracting water from the environment and from the lower layers of skin (dermis) and increasing the amount of water in the surface layers of skin. Another aspect of glycerin's benefit is that it is a skin-identical ingredient, meaning it is a substance found naturally in skin. In that respect it is one of the many substances in skin that help maintain the outer barrier and prevent dryness or scaling. The Food and Drug Administration (FDA) includes glycerin on its list of direct food additives considered Generally Recognized As Safe (GRAS), and on its list of approved indirect food additives. Glycerin is also an FDA-approved active ingredient in Over-the-Counter (OTC) skin protectant drug products and ear drying products, and it is an approved demulcent for the eyes.

Cetyl palmitate acts as an emollient, acting as a lubricant on the skin's surface, which gives the skin a soft and smooth appearance. The palmitates generally are esters of palmitic acid and ethylhexyl, cetyl, or isopropyl alcohol. In cosmetics and personal care products, they all function as skin conditioning agents and emollients. The palmitates are efficient opacifiers in cream and lotion shampoos. Isopropyl Palmitate also functions as a binder. The safety of the palmitates has been assessed by the Cosmetic Ingredient Review (CIR) Expert Panel. The CIR Expert Panel evaluated the scientific data and concluded that Ethylhexyl Palmitate, Cetyl Palmitate and Isopropyl Palmitate were safe as cosmetic ingredients. In 2001, the CIR Expert Panel considered available new data on Ethylhexyl, Cetyl and Isopropyl Palmitate and reaffirmed the above conclusion.

Light mineral oil acts as an emollient, skin protectant, and solvent. Mineral oil functions as an emollient skin conditioning agent, an occlusive skin protectant, and as a solvent. The FDA permits the use of mineral oil as an active ingredient in the following OTC drug product categories: anorectal drugs, skin protectants, and ophthalmic emollients.

Caprylic/capric triglyceride (CAS No. 124-07-2) acts as a moisturizer, viscosity modulator, inactive carrier, and stabilizer. Caprylic/capric triglyceride is an oily liquid made from coconut oil. It is used in cosmetics and other personal care products, such as face creams, lipstick, eye makeup and foundations. It can also be used in perfumes, moisturizers and sunscreens. It is found naturally in foods but can also be made by industrial processes. Caprylic/capric triglyceride has a number of useful properties in the formulation of cosmetics and, in particular, face creams. Caprylic/capric triglyceride creates a barrier on the skin's surface, decreasing the amount of moisture lost through the skin, functioning not only to prevent dryness in skin, but also as a skin conditioning agent. It provides a slippery feeling and promotes dispersion of pigments in various colored cosmetics. Caprylic/capric triglycerides have a low viscosity. This property allows it to alter the thickness of a particular cosmetic product. Adding caprylic/capric triglycerides to thick face creams helps thin them out to the desired thickness. Caprylic/capric trigylceride does not readily oxidize. It is particularly useful as a stabilizer of emulsions. This property is particularly useful in facial creams and other cosmetic products, helping to give them a longer shelf life. The Food and Drug Administration lists caprylic/capric triglyceride as Generally Recognized As Safe, or GRAS, for use as a direct food additive. In addition, caprylic/capric triglyceride has been assessed by the Cosmetic Ingredient Review Expert Panel, which evaluated the scientific data and concluded, and reaffirmed in 2001, that it was safe as it was being used at that time. Similarly suitable triglyceride materials include medium-chain triglyceride oil (CAS 65381-09-1) available as MCT oil from Acme-Hardesty Oleochemicals.

Octyldodecanol (CAS No. 5333-42-6; Tegosoft® G20 available from Evonik) acts as a stabilizer, emulsifier, lubricant, and solvent. Octyldodecanol helps to form emulsions and prevent an emulsion from separating into its oil and liquid components. These ingredients also reduce the tendency of finished products to generate foam when shaken. When used in the formulation of skin care products, octyldodecanol acts as a lubricant on the skin surface, which gives the skin a soft, smooth appearance. The safety of Octyldodecanol and related ingredients has been assessed by the Cosmetic Ingredient Review (CIR) Expert Panel. The CIR Expert Panel evaluated the scientific data and concluded that octyldodecanol was safe for use in cosmetics and personal care products. In 2004, the CIR Expert Panel considered available new data on octyldodecanol and reaffirmed the above conclusion. Octyldodecanol may be used in cosmetics and personal care products marketed in Europe according to the general provisions of the Cosmetics Directive of the European Union.

Cetyl alcohol (CAS No. 36653-82-4) acts as an emollients, thickeners, and emulsifier. Cetyl alcohol and the other fatty alcohols keep an emulsion from separating into its oil and liquid components. These ingredients are also used to alter the thickness of liquid products and to increase foaming capacity or to stabilize foams. The safety of cetyl alcohol has been assessed by the Cosmetic Ingredient Review (CIR) Expert Panel. The CIR Expert Panel evaluated the scientific data and concluded that this fatty alcohol was safe for use as a cosmetic ingredient. In 2005, the CIR Expert Panel considered available new data on cetearyl alcohol and the other fatty alcohols and reaffirmed the above conclusion. If they are derived from plants, cetearyl, cetyl, isostearyl, myristyl and behenyl alcohols may be used in cosmetics and personal care products marketed in Europe according to the general provisions of the Cosmetics Directive of the European Union. Ingredients of animal origin must comply with European Union animal by-products regulations.

Glyceryl stearate (CAS Nos. 11099-07-3, 31566-31-1) may act as an emulsifier, humectant, lubricant, or solvent. As an emulsifier it assists in forming neutral, stable emulsions; it is also a solvent, humectant, and consistency regulator in water-in-oil and oil-in-water formulations. It is typically derived from palm kernel or soy oil for cosmetic use. Glyceryl stearate helps to form emulsions by reducing the surface tension of the substances to be emulsified. The safety of Glyceryl Stearate has been assessed by the Cosmetic Ingredient Review (CIR) Expert Panel. The CIR Expert Panel evaluated the scientific data and concluded that Glyceryl Stearate was safe for use in cosmetics and personal care products. The CIR Expert Panel reviewed chronic studies of glyceryl stearate that showed no adverse effects on reproduction, and no carcinogenic effects. Human exposure studies of products containing glyceryl stearate and glyceryl stearate SE, as well as clinical experience, have shown these compounds to be non-sensitizing, non-phototoxic and non-photosensitizing. If they are made from plants, glyceryl stearate and glyceryl stearate SE may be used in cosmetics and personal care products marketed in Europe according to the general provisions of the Cosmetics Directive of the European Union. Ingredients made from animal sources must comply with the European Union animal by-products regulations. A suitable material is available from Protameen Chemicals Inc. under the trade name "Protachem GMS-450."

Colloidal oat flour (CAS No. 281-672-4) may act as a moisturizer, skin protectant, pH buffer, and anti-inflammatory agent, and may have anti-irritant and anti-inflammatory properties. As a skin protectant, colloidal oatmeal temporarily protects injured or exposed skin from harmful or annoying stimuli, and may therefore provide relief to the skin. Oatmeal has been used for centuries as a soothing agent to relieve itch and irritation associated with various xerotic dermatoses. In 1945, a ready to use colloidal oatmeal, produced by finely grinding the oat and boiling it to extract the colloidal material, became available. Today, colloidal oatmeal is available in various dosage forms from powders for the bath to shampoos, shaving gels, and moisturizing creams.

Currently, the use of colloidal oatmeal as a skin protectant is regulated by the U.S. Food and Drug Administration (FDA) according to the Over-The-Counter Final Monograph for Skin Protectant Drug Products issued in June 2003. Its preparation is also standardized by the United States Pharmacopeia. The many clinical properties of colloidal oatmeal derive from its chemical polymorphism. The high concentration in starches and beta-glucan is responsible for the protective and water-holding functions of oat. The presence of different types of phenols confers antioxidant and anti-inflammatory activity. Some of the oat phenols are also strong ultraviolet absorbers. The cleansing activity of oat is mostly due to saponins. Its many functional properties make colloidal oatmeal a cleanser, moisturizer, buffer, as well as a soothing and protective anti-inflammatory agent.

The Food and Drug Administration (FDA) reviewed the safety and efficacy of colloidal oatmeal and approved its use as an active ingredient in Over-the-Counter (OTC) skin protectant drug products at a minimum concentration of 0.007%, or 0.003% when used in combination with mineral oil. When used as a skin protectant in an OTC skin protectant drug product, this ingredient must be called colloidal oatmeal. The Cosmetic Ingredient Review (CIR) has deferred evaluation of this ingredient because the safety has been assessed by FDA. This deferral of review is according to the provisions of the CIR Procedures. *Avena Sativa* (Oat) Kernel Meal and colloidal oatmeal may be used in cosmetics and personal care products marketed in Europe according to the general provisions of the Cosmetics Directive of the European Union.

Dimethicone (CAS No. 9006-65-9) may act as a moisturizer and emollient. Dimethicone is a silicone based polymer that forms a protective barrier on the skin to help retain moisture. Dimethicone's oil-like consistency also gives it emollient properties. The Food and Drug Administration (FDA) reviewed the safety of dimethicone and approved its use as a skin protectant active ingredient in over-the-counter (OTC) drug products. The safety of Dimethicone has been assessed by the Cosmetic Ingredient Review (CIR) Expert Panel. The CIR Expert Panel evaluated the scientific data and concluded that these ingredients were safe for use in cosmetics. Dimethicone, methicone, and the related polymers may be used in cosmetics and personal care products marketed in Europe according to the general provisions of the Cosmetics Directive of the European Union. The World Health Organization Joint FAO/WHO Expert Committee on Food Additives has established an acceptable daily intake level for Dimethylpolysiloxane (Dimethicone) of 0 to 1.5 mg/kg body weight.

PEG-40 stearate (CAS No. 9004-99-3) may act as an emulsifier. PEG-40 stearate typically functions as a cleansing agent, but also helps keep ingredients solubilized. Suitable materials include a PEG-40 stearate available from Lipo Chemicals Inc. under the trade name "Lipopeg® 39S." The safety of the PEG stearates has been assessed by the Cosmetic Ingredient Review (CIR) Expert Panel. The CIR Expert Panel evaluated the scientific data and concluded that PEG-2, -6, -8, -12, -20, -32, -40, -50, -100 and -150 stearates are safe for use in cosmetics and personal care products. In 2002, as part of the scheduled re-evaluation of ingredients, the CIR Expert Panel considered available new data on the PEG Stearates and reaffirmed the above conclusion. In the CIR Safety Review, the PEG stearates, whose average number of ethylene oxide monomers range from 2 to 150, were nonlethal at levels up to 10 g/kg. They gave evidence of only minimal skin irritation and minimal eye irritation when tested at 100%. PEG-8, -40 and -100 stearates produced no significant changes in growth, histopathologic observations or hematologic values in long-term feeding studies. Multiple generation studies of PEG-8 and -40 stearates were negative for effects on reproduction. Clinical studies on the PEG stearates indicated that these ingredients were neither irritants nor sensitizers at concentrations of 25% or greater. There was no evidence of phototoxicity or photosensitization of PEG-2 or -8 stearates. Because the smaller PEG stearates were not photosensitizing the CIR Expert Panel did not expect the larger ingredients to be photosensitizing. The CIR Expert Panel concluded that safety data on individual PEG stearates were sufficient for a decision regarding the safety of the entire group.

Carbomer polymers may act a thickeners and formulation stabilizers. Carbomers are synthetic polymers of varying molecular weights that can be used to thicken suspend and stabilize cosmetic formulations. Requiring very low concentrations, carbomers are often used to adjust the viscosity of cosmetic preparations. They dry quickly and are not film forming. Carbomers as an ingredient family resist bacterial attack and do not readily support mold growth. Under normal conditions, gels prepared with sodium carbomer neither prevent nor promote the growth of microorganisms;

therefore the addition of a suitable preservative system is advisable. The safety of the Carbomer has been assessed by the Cosmetic Ingredient Review (CIR) Expert Panel. The CIR Expert Panel evaluated the scientific data and concluded that carbomer polymers were safe as ingredients in cosmetics and personal care products. In 2001, as part of the scheduled re-evaluation of ingredients, the CIR Expert Panel considered available new data on carbomer polymers and reaffirmed the above conclusion.

The CIR Expert Panel reviewed acute oral studies showing that carbomer polymers have low toxicities when ingested. Minimal skin irritation and no to moderate eye irritation were observed. Subchronic feeding studies with a carbomer polymer resulted in lower than normal body weights, but no abnormal changes were observed in the organs. Some gastrointestinal irritation and marked pigment deposition within specific cells in the liver, called Kupffer cells, were seen in studies with carbomer. Clinical studies with carbomers showed that these polymers have low potential for skin irritation and sensitization at concentrations up to 100%. A carbomer polymer demonstrated low potential for phototoxicity and photo-contact allergenicity. The Carbomers may be used in cosmetics and personal care products marketed in Europe according to the general provisions of the Cosmetics Directive of the European Union.

Sodium Hydroxide (CAS No. 1310-73-2) may function as a pH modulator, an alkali used to neutralize acids in maintenance of pH of the cream. The Food and Drug Administration (FDA) includes sodium hydroxide on its list of substances affirmed as Generally Recognized as Safe (GRAS) for direct addition to food. Sodium hydroxide, as well as calcium hydroxide, is also approved as an indirect food additive for use as a defoaming agent in the manufacture of paper and paperboard used as food packaging. Sodium hydroxide is listed in the Cosmetics Directive of the European Union (see Annex III) and may be used at the following concentrations and pH values: 5% by weight in nail cuticle solvents, 2% by weight in hair straighteners for general use, 4.5% by weight in hair straighteners for professional use, up to a pH 12.7 in depilatories, and up to pH 11 in other uses as a pH adjuster. The nail cuticle solvents and the general use hair straighteners containing these ingredients must be labeled "contains alkali, avoid contact with eyes, can cause blindness, keep out of reach of children." The professional hair straighteners must be labeled "for professional use only, avoid contact with eyes, can cause blindness." Depilatories containing these ingredients must include the following on the label: "Keep out of reach of children, avoid contact with eyes."

Phenoxy ethanol (CAS No. 9004-78-8) may act as a preservative, anti-oxidant, or anti-microbial. Phenoxyethanol is used as a preservative in cosmetics. Phenoxyethanol prevents or retards microbial growth, and thus protects cosmetics and personal care products from spoilage. It may also be used in fragrances. Phenoxyethanol is usually synthesized for commercial use but it can also be found naturally in products such as green tea. The CIR Expert Panel reviewed safety data on phenoxyethanol and noted that it was practically nontoxic via oral and dermal administration. In a subchronic oral study, increased weights of some organs were noted when high doses of phenoxyethanol were administered. The doses in this study were considered to be much higher than those resulting from use of cosmetics and personal care products containing phenoxyethanol. In dermal laboratory studies, phenoxyethanol did not cause any birth defects. Phenoxyethanol was not mutagenic. In clinical studies, phenoxyethanol was neither a primary nor a cumulative irritant, it did not cause delayed hypersensitivity, and was it nonphototoxic. Phenoxyethanol is listed as 2-Phenoxyethanol in Annex VI, Part 1 (preservative which cosmetic products may contain) of the Cosmetics Directive of the European Union and may be used in concentrations up to 1%.

Caramel Coloring III (CAS No. 8028-89-5) is a coloring agent derived from heating edible sugar. In cosmetics and personal care products, caramel is used in the formulation of a wide variety of product types as a coloring agent. The Food and Drug Administration (FDA) includes caramel on its list of substances considered Generally Recognized As Safe (GRAS) as a multipurpose food substance. FDA also lists caramel as a color additive exempt from certification. Caramel is determined to be safe for use in coloring cosmetics and personal care products, including products applied to the lips and area of the eye. The Cosmetic Ingredient Review (CIR) has deferred evaluation of this ingredient because the safety has been assessed by FDA. This deferral of review is according to the provisions of the CIR Procedures. Caramel functions as a colorant in cosmetics and personal care products. To be used as a colorant in the United States, caramel must comply with FDA manufacturing requirements. For example, only certain food-grade acids, alkalis, and salts may be used to assist carmelization, in amounts consistent with good manufacturing practice. Caramel is listed in Annex IV, Part I (coloring agent allowed for use in cosmetic products) of the Cosmetics Directive of the European Union and may be used without restriction when purity requirements included in food regulations are fulfilled.

DMDM Hydantoin (e.g., Glydant® Plus available from Lonza) may function as a preservative and anti-microbial. It is used as an antimicrobial formaldehyde releaser preservative with the trade name Glydant. DMDM hydantoin is an organic compound belonging to a class of compounds known as hydantoins. It is used in the cosmetics industry and found in products like shampoos, hair conditioners, hair gels and skin care products. DMDM hydantoin works as a preservative because the released formaldehyde makes the environment less favorable to the microorganisms. The Cosmetic Ingredient Review (CIR) Expert Panel has evaluated DMDM hydantoin and concluded that it was safe to a great majority of consumers but has limited the concentration to 0.2% free formaldehyde due to the skin sensitivity of some individuals to this agent. A study found "[a]n increase in the use of DMDM hydantoin in cosmetic products will also inevitably increase the risk of cosmetic dermatitis in consumers allergic to formaldehyde."

The CIR Safety Review determined DMDM hydantoin is poorly absorbed from the skin. In a laboratory study, oral exposure to DMDM hydantoin did not result in any adverse effects. The CIR Expert Panel noted that DMDM hydantoin is a formaldehyde donor in aqueous media. They attributed positive results in some in vitro mutagenicity studies to formaldehyde release. In these studies, the concentrations of DMDM hydantoin tested were higher than those used in cosmetic and personal care products, likely resulting in much higher concentrations of formaldehyde than found in products. Clinical studies revealed some observations of skin irritation which could also be related to the release of formaldehyde from DMDM hydantoin. The CIR Expert Panel has reviewed the safety of formaldehyde in cosmetics and personal care products and concluded that it was safe to a great majority of consumers but has limited the concentration to 0.2% free formaldehyde due to the skin sensitivity of some individuals to this agent. The amount of DMDM hydantoin required to preserve a product (less than 1%) does not expose the consumer to concentrations of formaldehyde above the 0.2% limit for formaldehyde recommended by the CIR Expert Panel.

DMDM hydantoin, called dimethylol, dimethylhydantoin [1,3-Bis(hydroxymethyl)-5,5-dimethylimidazolidine-2,4-dione], is listed in Annex VI, Part I (preservatives which cosmetics products may contain) of the Cosmetics Directive of the European Union and may be used in cosmetics and personal care products at a maximum concentration of 0.6%. If the concentration of released formaldehyde exceeds 0.05% in the finished product it must be labeled "contains formaldehyde."

Iodopropynyl Butylcarbamate (CAS No. 55406-53-6) may function as a preservative, anti-microbial, and anti-fungal. The active ingredient of this product, IPBC, is recognized by the CTFA in the USA for use in cosmetic and personal care products and listed by the EU as an approved cosmetic preservative. IPBC-II is a colorless to light yellow, clear viscous liquid at room temperature. It is a unique and cost effective preservative that provides a high level of antimicrobial activity. It is remarkably proficient in inhibiting the growth of yeasts and molds. IPBC is compatible with essentially all cosmetic ingredients, such as surfactants, emulsifiers, proteins and herbal extracts.

Methods of Preparation

The compositions in general are prepared from the imidazole compound and colloidal oatmeal, as well as any other desired benefit agents. If desired additional ingredients such as surfactants and emulsifying agents, antihistamines, topical anesthetics, topical antipruritics, astringents, and emollients may be added. The ingredients may be added in such steps and amounts and processing varied as to create a spray, cream, gel, ointment, or lotion.

The advantages of the invention and specific embodiments of the skin care compositions prepared in accordance with the present invention are illustrated by the following examples. It will be understood, however, that the invention is not confined to the specific limitations set forth in the individual examples, but rather defined within the scope of the appended claims.

EXAMPLES

Example 1

A topical formulation containing 100 mg of THI in 10 g of base cream was prepared as follows. To 1.0 g of base cream (water, glycerin, mineral oil, cetyl palmitate, caprylic/capric triglyceride, octyldodecanol, cetyl alcohol, glyceryl stearate, colloidal oat flour, dimethicone, PEG-40 stearate, carbomer, sodium hydroxide, phenoxy ethanol, caramel III coloring, DMDM hydantoin, iodopropynyl butylcarbamate) was added 100 mg of THI (CAS No. 94944-70-4) portionwise with levigation of the powder between additions. A smooth cream was obtained by levigation in a marble mortar and pestle. A dime-sized portion of the levigated material was then incorporate geometrically with similar-sized portions of base and mixed thoroughly. Geometric mixing with additional cream base was repeated until 9.9 g of base was incorporated, yielding a 1.0% THI cream. Examination of the cream on a mixing plate suggested the THI was at least partially dissolving in the cream base. Application of the finished cream to the skin left no residue.

Example 2

Eczema/Psoriasis Lotion Treatment

The treatment test regime consists of three concentrations ranging from 0.5% to 2% of the active ingredient THI. Affected areas are documented with before and after photos and notes of observations from each step in the treatment regime are recorded. Three lotions respectively containing 0.5% (Disc "A"), 1.0% (Disc "B"), and 2% (Disc "C") by weight of THI are used in the treatment test.

Standard Application Protocol

The area to which the lotion is to be applied to is cleaned before starting treatment. The lotion from Disc "A" is applied to just cover the affected area twice a day, once in morning and once again in evening. Any physical changes observed are noted; the treatment is discontinued if redness occurs. This regime is continued for one week. If the desired effect is realized at this concentration, applications at 0.5% concentration are continued without moving on to the next higher concentration. The treatment is discontinued if redness occurs.

At the start of week two if no observed relief is noticed with 0.5% lotion from Disc "A", treatment is begun with 1.0% lotion from Disc "B". The application regime just described is repeated substituting the 1.0% lotion from disc "B" for one week. If the desired effect is realized at 1.0% concentration, the applications are continued at this concentration without moving on to the next higher concentration. Any physical changes observed are noted; the treatment is discontinued if redness occurs.

At the start of week three if no observed relief is noticed with 1.0% lotion from Disc "B", treatment is begun with 2.0% lotion from Disc "C". The application regime just described is repeated substituting the 2.0% lotion from disc "C" for one week. If the desired effect is realized at 2.0% concentration, the applications are continued at this concentration. Any physical changes observed are noted; the treatment is discontinued if redness occurs.

Example 3

Test Case for Excema

The subject is a 10-year-old Caucasian male, in otherwise excellent health, suffering from excema over a portion of the subject's thighs. The subject rated the severity of the excema before treatment according to the protocol of Example 2 as 9 on a scale of 0 to 10, where 0 represents no psoriasis or excema, and 10 represents extremely bad psoriasis or excema. The subject had been previously treated with locoid lipid oil and hyderm topical hydrocortisone treatments with little to moderate success. The subject rated the effectiveness of the locoid lipid oil as 2 and of the hyderm cream as 4 on a scale of 1 to 5, where 1 represents an extremely useful treatment, and 5 represents no change in symptoms. After following the treatment protocol of Example 2 using only the 0.5% concentration lotion, the subject rated the severity of excema after treatment as 0.

Example 4

Test Case for Psoriasis

The subject is a 63-year-old Caucasian male, apparently in otherwise good health, suffering from psoriasis over a portion of the subject's chest and lower back. The subject had been suffering from moderate to severe psoriasis in these areas for more than 40 years and was able to obtain only moderate relief during that time from a variety of treatments including UV radiation, and at the time immediately prior to the treatment according to the protocol of Example 2 had been taking methotrexate orally and applying Daivonet or Daivonex ointments topically. Following the treatment protocol of Example 2 for two weeks and three weeks concluding with the 2.0% concentration lotion substantially relieved the subject's psoriatic symptoms.

What is claimed:

1. A method of treating, managing, or preventing a dermatological or skin condition, which comprises topically administering to a human subject in need thereof a therapeutically or prophylactically effective benefit agent comprising colloidal oatmeal and 2-acetyl-4-tetrahydroxybutylimidazole or a pharmaceutically, dermatologically, or cosmetically acceptable salt thereof, wherein the benefit agent comprises 0.01% to 10% by weight of the 2-acetyl-4-tetrahydroxybutylimidazole or a pharmaceutically, dermatologically, or cosmetically acceptable salt thereof and 0.01% to 25% by weight of the colloidal oatmeal.

2. The method of claim 1, wherein the dermatological or skin condition is an immune-mediated skin condition.

3. The method of claim 2, wherein the immune-mediated skin condition is atopic dermatitis, seborrheic dermatitis, contact dermatitis, cutaneous sarcoidosis, drug induced photosensitivity, fixed drug eruptions, id reactions, bullous skin diseases, discoid lupus erythematosus, subacute cutaneous lupus, alopecia areata, sea bather's eruptions, eczema, or psoriasis.

4. The method of claim 1, wherein the dermatological or skin condition is atopic dermatitis, seborrheic dermatitis, contact dermatitis, cutaneous sarcoidosis, drug induced photosensitivity, fixed drug eruptions, id reactions, bullous skin diseases, discoid lupus erythematosus, subacute cutaneous lupus, alopecia areata, sea bather's eruptions, eczema, or psoriasis.

5. The method of claim 1, wherein the dermatological or skin condition is an inflammatory or immune-mediated dermatosis.

6. The method of claim 5, wherein the inflammatory or immune-mediated dermatosis is atopic dermatitis.

7. The method of claim 5, wherein the inflammatory or immune-mediated dermatosis is a papulosquamous dermatosis.

8. The method of claim 7, wherein the papulosquamous dermatosis is psoriasis.

9. A method of caring for skin, delivering or depositing a benefit agent onto skin, or suppressing a dermatologic immune response in a patient in need thereof, which comprises topically administering to the skin of a human subject in need thereof a benefit agent comprising colloidal oatmeal and 2-acetyl-4-tetrahydroxybutylimidazole or a pharmaceutically, dermatologically, or cosmetically acceptable salt thereof, contained in a dermatologically acceptable carrier, wherein the benefit agent comprises 0.01% to 10% by weight of the 2-acetyl-4-tetrahydroxybutylimidazole or a pharmaceutically, dermatologically, or cosmetically acceptable salt thereof and 0.01% to 25% by weight of the colloidal oatmeal.

10. The method of claim 1, wherein the benefit agent comprises 0.1% to 5% by weight of 2-acetyl-4-tetrahydroxybutylimidazole or a pharmaceutically, dermatologically, or cosmetically acceptable salt thereof and 0.1% to 10% by weight of the colloidal oatmeal.

11. The method of claim 1, wherein the benefit agent comprises 0.5% to 2% by weight of 2-acetyl-4-tetrahydroxybutylimidazole or a pharmaceutically, dermatologically, or cosmetically acceptable salt thereof and 0.5% to 2% by weight of the colloidal oatmeal.

12. The method of claim 9, wherein the caring for skin comprises cleansing and/or moisturizing.

* * * * *